United States Patent [19]

Isowa et al.

[11] 4,086,136
[45] Apr. 25, 1978

[54] PROCESS FOR PRODUCING A PEPTIDE USING A SERINE OR THIOL PROTEINASE

[75] Inventors: Yoshikazu Isowa; Muneki Ohmori, both of Tokyo; Hideaki Kurita, Sagamihara; Tetsuya Ichikawa, Sagamihara; Masanari Sato, Sagamihara; Kaoru Mori, Sagamihara, all of Japan

[73] Assignee: (Zaidanhojin) Sagami Chemical Research Center, Tokyo, Japan

[21] Appl. No.: 732,543

[22] Filed: Oct. 14, 1976

[51] Int. Cl.² ............................................. C12D 13/06
[52] U.S. Cl. ...................................... 195/29; 195/30; 260/112.5 R
[58] Field of Search .......................... 195/29, 30, 2, 4; 260/112.5

[56] References Cited

U.S. PATENT DOCUMENTS 3,972,773  8/1976  Isowa et al. ........................... 195/29

OTHER PUBLICATIONS

Jones et al., "Transamidation Reactions Catalyzed by Cathepsin C", *Journal of Biological Chemistry*, vol. 195, (1952), pp. 645–656.
Fruton et al., "Synthesis of Polymeric Peptides in Proteinase Catalyzed Transamidation Reactions", *Journal of Biological Chemistry*, vol. 204, (1953), pp. 891–902.
Johnston et al., "Catalysis of Transamidation Reactions by Proteolytic Enzymes", *Journal of Biological Chemistry*, vol. 185, (1950), pp. 629–641.

*Primary Examiner*—Raymond N. Jones
*Assistant Examiner*—Thomas G. Wiseman
*Attorney, Agent, or Firm*—Oblon, Fisher, Spivak, McClelland & Maier

[57] ABSTRACT

A peptide having the formula

X—A—B—Y— wherein A and B are the same or different and each represents an amino acid residue or a peptide residue, X represents an amino protective group, Y represents a carboxyl protective group selected from the group consisting of tertiary alkoxy, and benzyloxy, benzylamino and benzhydrylamino which can be substituted with an inert substituent, is prepared by a process which comprises reacting an amino acid or peptide having an N-terminal protective group, or a salt thereof of the formula:

X—A—OH with an amino acid or peptide having a C-terminal protective group or a salt thereof of the formula:

H—B—Y in the presence of a thiol proteinase or serine proteinase enzyme in an aqueous solution having a pH sufficient to maintain the enzyme activity of said thiol proteinase or serine proteinase.

10 Claims, No Drawings

PROCESS FOR PRODUCING A PEPTIDE USING A SERINE OR THIOL PROTEINASE

BACKGROUND OF THE INVENTION

1. Field of the Invention

The present invention relates to a process for producing a peptide. More particularly, it relates to a process for producing a peptide by using a specific enzyme as a catalsyt.

2. Description of the Prior Art

Typical conventional processes for producing peptides include the azide method, the mixed acid anhydride method, the carbodiimide method, the active ester method and the acid chloride method and the like. However, various industrial problems are encountered by these conventional processes, such as racemization of the carboxyl component of the C-terminal amino acid residue occurs. Other problems include side reactions, temperature control, selection of solvent, the properties of amino protective groups and carboxyl protective groups and the effects of functional groups on the side chains of amino acids. The fragment condensation method of preparing peptides can be applied to advantage for compounds which contain glycine (the only amino acid which cannot be racemized) at the carboxyl terminal group. However, for compounds containing any other amino acid at the carboxyl terminal group the racemization cannot be prevented. In actuality, an in any peptide synthesis, the racemization problem is serious. When racemization occurs, the purity of the product is decreased and it is necessary to separate the impure isomer from the product. This is very detrimental for any industrial operation.

Among the conventional methods for forming peptide bonds, the azide method is the only method in which racemization is not much of a problem and it is for this reason that it is a desirable method. However, the azide method involves complicated operational procedures and an urea derivative is produced in a side reaction. Because of these features the azide method is undesirable from the viewpoint of yield. In addition to the various organic chemical processes, for preparing peptides, a particular peptide synthesis using the enzyme papain or chymotrypsin has been disclosed (See, for example, J. S. Fruton "Advances in Protein Chemistry", 5, Academic Press Inc. New York, N.Y. 1949).

The reactions of the method are as follows:

Bz-Leu-OH + H-Leu-NHφ    (1)
 (I)       (II)
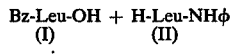 Bz-Leu-Leu-NHφ
           (III)
Bz-Leu-OH + H-Gly-NHφ    (2)
 (I)       (II)
 Bz-Leu-Gly-NHφ
           (III)
Bz-Tyr-OH + H-Gly-NHφ    (3)
 (I)       (II)
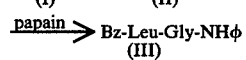 Bz-Tyr-Gly-NHφ
           (III)
Z-Phe-Gly-OH + H-Tyr-NH₂    (4)
 (I)          (II)
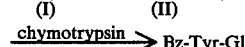 Z-Phe-Gly-Tyr-NH₂
           (III)

A problem common to the processes of reactions (1)–(3) is that it is necessary to remove the phenylamino group from the peptide (III) under severe conditions because the phenylamino group which is bonded to the C-terminal group of the amine component (II) cannot be easily separated from the peptide, and thus some disadvantageous cleavage of the peptide chain occurs. Because of this deficiency, this mode of peptide synthesis cannot be practically used for peptide synthesis. On the other hand, reaction (4) is accompanied by transamidation and transpeptidation side reactions and thus is not practically suitable. (See, for example, R. B. Johnston et al; J. Biol. Chem., 185, 629(1950) and J. S. Fruton et al; J. Biol. Chem. 204,891(1953). In reaction (4), the primary amino group of the acid amide bonded to the terminal group of the amine component, promotes the papain catalyzed amidase reaction. Accordingly, these processes provide only a theoretical interest in showing that papain and chymotrypsin act as catalysts for the synthesis of peptide bonds in which the phenylamino group is used as the protective group for the terminal carboxyl group of the amine component.

A need, therefore, continues to exist for a method of peptide synthesis in which the variety of difficulties encountered by the prior art procedures can be overcome.

SUMMARY OF THE INVENTION

Accordingly, one object of the present invention is to provide a process for synthesizing a desired oligopeptide or polypeptide by a simple operation in high yield.

Briefly, this object and other objects of the invention as hereinafter will become more readily apparent can be attained in a process for producing a peptide having the formula:

$$X-A-B-Y$$

wherein A and B are the same or different and represent an amino acid residue or a peptide residue, X represents an amino protective group, Y represents a carboxyl protective group selected from the group consisting of substituted or unsubstituted tertiary alkoxy, and benzyloxy, benzylamino and benzhydrylamino, by reacting an amino acid or peptide having an N-terminal protective group or a salt thereof of the formula $$X-Z-OH$$

with an amino acid or peptide having a C-terminal protective group or a salt thereof of the formula $$H-B-Y$$

in the presence of a thiol proteinase or serine proteinase enzyme in an aqueous solution having a pH sufficient to mantain the enzyme activity of said thiol proteinase or serine proteinase.

DESCRIPTION OF THE PREFERRED EMBODIMENTS

Typical thiol proteinase enzymes include papain, Stembromelein, Ficin, Cathepsin B, Chymopapain, Streptococcal proteinase, Asclepain, Clostridium histolyticum proteinase B and Yeast proteinase B. Thiol proteinases are characterized by their ability to hydrolyze a wide range of proteins and to promote the cleavage of many peptide bonds, amide bonds and ester bonds as well as to promote the decomposition of benzoyl arginine amide, benzoyl glycylleucylglycine and benzol tyrosylglycine amide thereby showing both exo and endo peptidase activity (J. R. Kimmel and E. L.

Smith, Advances in Enzymology, 19, 267 (1957). Typical serine proteinases include Subtilisin, Aspergillus alkaline proteinase, Elastase, α-Lytic proteinase, Chymotrypsin, Metridium proteinase A, Trypsin, Thrombin, Plasmin, Kininogenin, Enteropeptidase, Acrosin, Phaseolus proteinase, Altemaria endopeptidase, Arthrobacter serine protenase and Tenebrio α-proteinase. It has been reported that the serine proteinase has substantial hydrolysis activity to the Leu (15) - Tyr (16) and Tyr (16) - Leu (17) sequence of the insulin B chain and also exhibits high esterase activity to acylamino acid esters. The subtilisin produced by using B. Subtilis or analogous germs includes types of Carsbery, Novo, BPN' and the like. The alkaline proteinase isolated from ray fungus or fungi is a known material. The amino acid or peptide starting materials having the formula

X—A—OH wherein X represents a protective group for the terminal amino group and A represents an amino acid residue or a peptide residue, which is used in the process of the invention are referred to as the acid component. The radical A in the formula more definitely represents an amino acid residue or peptide residue wherein suitable amino acids include aliphatic amino acids such as monoamino monocarboxylic acids, e.g. glycine (Gly), alanine (Ala), valine (Val), norvaline (nor-Val), leucine (Leu), isoleucine(iso-Leu), norleucine(nor-Leu); oxyamino acids, e.g. serine (Ser), threonine (Thr), homoserine(homo-Ser); sulfur-containing amino acids, e.g. methionine (Met) or cystine (CysS) and cysteine (CysH); monoamino dicarboxylic acids, e.g. aspartic acid (Asp), glutamic acid (Glu), asparagine (Asn) and glutamine (Gln); diamino monocarboxylic acids, e.g. ornithine (Orn), lysine (Lys), arginine (Arg); aromatic amino acids, e.g. phenylalanine (Phe), and tyrosine (Tyr); and heterocyclic amino acids, e.g. histidine (His), tryptophan (Try). (These amino acids are designated by symbols which are commonly used in the field.) (The peptides are also designated by combinations of these symbols).

Suitable protective groups for the free terminal amino group (an N-terminal protective group) of the acid component include tertiary alkoxycarbonyl groups such as t-butyloxycarbonyl (BOC-), t-amyloxycarbonyl (t-Aoc-); benzyloxycarbonyl (Z-), p-methoxybenzyloxycarbonyl (PMZ), 3,5-dimethoxybenzyloxycarbonyl {Z(OMe)$_2$-}, 2,4,6-trimethylbenzyloxycarbonyl (TMZ-), p-phenylazobenzyloxycarbonyl (PZ-); p-toluenesulfonyl (Tos-); o-nitrophenylsulfenyl (Nps-); and the like. The other amino acid or peptide starting material having the formula

H—B—Y which is used in the process of the invention is referred to as the amine component. In the formula, B represents an amino acid residue or peptide residue which can be defined in the same way as A above. The protective groups for the carboxyl group (C-terminal protective groups) of the amino component include tertiary alkoxy groups such as t-butoxy (—OBu$^t$), benzyloxy (—OBzl), p-nitrobenzyloxy {—OBzl (p-NO$_2$)}, benzhydryloxy (-OBzh), benzylamino (—NHBzl), 2,4-dimethoxy benzylamino (—NHDMB), and benzhydrylamino (—NHBzh). These protective groups for the terminal carboxyl group of the amine component are resistant to esterase and amidase reactions which are caused by the thiol proteinase and serine proteinase enzymes.

The acid component and the amine component used in the process of the invention include the amino acid residues and peptide residues which have a functional group on a side chain. In most of these cases, it is preferable to protect the functional group with a protective group. Suitable protective groups for the ω-amino group (N$^ω$) can be N$^ω$-benzyloxycarbonyl (N$^ω$-Z), t-butoxycarbonyl (N$^ω$-BOC) and tosyl (N$^ω$-Tos). Suitable protective groups for the N-guanidino group (N$^G$) of Arg include nitro (N$^G$—NO$_2$), N$^G$-benzyloxycarbonyl (N$^G$—Z) and N$^G$. N$^G$-dibenzyloxycarbonyl (N$^G$—Z—Z). Suitable protective groups for imidazole rings (N$^{im}$) of His include N$^{im}$-benzyl (N$^{im}$—Bzl) and tosyl (N$^{im}$—Tos). Suitable protective groups for the ω-carboxyl group include ω-benzyloxy(-OBzl). Suitable protective groups for the hydroxyl group of aliphatic or aromatic oxyamino acids include aralkyl groups such as -benzyl (Bzl). Suitable S-protective groups of the mercapto group of CysH include the benzyl group (Bzl). The protective groups should be both stable in the main reaction and easily removable from the product without being involved in side reactions. The acid component and the amine component starting materials can have protective groups or the Nα-$_{amino}$ group of the amine component can be free or in the form of an inorganic or organic salt such as a hydrochloride, hydrobromide, oxalate, p-toluenesulfonate or acetate. In the process of the invention, the condensation reaction in which the peptide bond is formed can be conducted in an aqueous solution having a pH which maintains enzyme activity which is about 4 to 7.5 for the thiol proteinase and 6 to 9 for the serine proteinase.

There are two methods which can be employed to achieve the proper pH to maintain enzyme activity. One method is to conduct the condensation reaction in a buffer solution such as a citric acid buffer solution, McIlvaine buffer solution, Kolthoff buffer solution, tris-HCl buffer solution, or veronal buffer solution in which the acid component and the amine component are dissolved and the enzyme is added. The other method is to conduct the condensation reaction by maintaining the pH of the reaction mixture in the proper range to maintain enzyme activity by adding the acid or the base to the reaction mixture depending upon the pH detected.

The starting materials are usually used in a ratio of 0.8 to two moles, preferably one to 1.5 moles of the acid component per one mole of the amine component. If the starting materials are not too soluble in the aqueous medium, it is possible to improve the solubility of the reactants by adding a solvent such as an alcohol, e.g. methanol, or ethanol; dimethylformamide; dioxane; tetrahydrofuran; dimethylsulfoxide, or the like to the aqueous solution. The amount of the added solvent should be limited so as not to inhibit the activity of the enzyme in the reaction of the invention. If a solvent is employed, it is usually used in an amount of less than 1 part by weight, preferably 0.2 to 1.0 part by weight per one part by weight of water. The reaction of the invention is performed in an aqueous medium, and it is necessary to decrease the relative solubility C, the reaction product preferably to a sparingly soluble or insoluble state in the system.

The amount of thiol proteinase or serine proteinase enzyme employed is in a range of 10 to 500 mg, preferably 10 to 400 mg, especially 50 to 300 mg per 1 mmole of the amine component. An enzyme activator such as CysH, or a salt thereof or 2-mercaptoethanol or a salt thereof can also be added to the solution. The reaction temperature employed is usually in a range of 20° to 55° C, preferably 30° to 40° C which is sufficient to maintain enzyme activity. The reaction proceeds smoothly under these conditions for 1 to 24 hours. The reaction product precipitates from the reaction system and the reaction product can be easily isolated.

In accordance with the process of the invention, a minimum size dipeptide, oligo-peptide or polypeptide having the formula

X—A—B—Y can be easily produced by appropriately selecting the desired A and B radicals in the starting materials having the formulas X—A—OH and H—B—Y.

When the dipeptide derivative of lysyl lysine which is produced by the following reaction Z—Lys(Z)—OH + H—Lys(Z)—OBu$^t$ →
Z—Lys(Z)—Lys(Z)—OBu$^t$ wherein the Z-derivative produced by lysine whose ω-amino group is protected with the carbobenzoxyl group (Z—), is used as the acid component and a t-butyl ester is used as the amine component, the lysyl lysine whose amino group in the side chain is protected, can be obtained. When the dipeptide derivative containing arginine i.e. arginyl leucine which is produced by the following reaction Z—Arg(Z,Z)—OH + H—Leu—OBzh →
Z—Arg(Z,Z)—Leu—OBzh, wherein the tri-Z-arginine is produced by protecting the guanyl group and the amino group of arginine with Z, is used as the acid component and the benzhydryl ester of leucine is used as the amine component, a dipeptide derivative can be easily obtained by the reaction in the presence of papain. When an amino acid having a functional group in the side chain is used, the amino acid can be reacted with the functional group protected on unprotected as in the examples. Various reactions of histidine will be shown by the following reaction sequences.

BOC—His(Bzl)—OH + H-Leu-OBzh →
BOC—His(Bzl)—Leu—OBzh       (a)

BOC—His—OH + H—Leu—OBzh →
BOC—His—Leu—OBzh            (b)

Reaction (a) represents the situation in which the side chain is protected, and the reaction (b) represents the case in which the side chain is unprotected.

The dipeptide situation has been illustrated. Another situation is the case of the acid component which has one peptide bond and is represented by the reaction of an acyl dipeptide with an amino acid amide derivative. The reaction can be smoothly performed without the occurrence of side reactions in the presence of papain. This situation is shown by the following reaction.

Z—Pro—GLy—OH + H—Leu—NHBzh →
Z—Pro—Gly—Leu—NHBzh

The above reaction proceeds smoothly to form carbobenzoxy-prolyl-glycylleucine-benzhydrylamide.

Examples of the synthesis of tripeptides are shown in Table 3. The situation in which the acid component is a dipeptide and the amine component is a dipeptide will now be illustrated. The following reaction can be applied for the synthesis of fragment (3-6) tetrapeptide of Val$^5$-angiotensin-II which is known as a polypeptide hormone BOC—Val—Tyr(Bzl)—OH +
H—Val—His(Bzl)—OBzl →
BOC—Val—Tyr(Bzl)—Val—His(Bzl)—OH When valyl histidine ester is used as the amine component of the reaction and the reaction is performed in the presence of papain, a tetrapeptide containing a benzyl ester group cannot be obtained. This is believed to be the result of an esterase action which is one of the characteristics of papain. The above reaction is especially advantageous when the tetrapeptide is used as the acid component in the next step of a polypeptide synthesis. When the carboxyl group of the amine component is the benzhydryl amide, a tetrapeptide benzhydrylamide derivative can be obtained in high yield. Examples in which a dipeptide derivative is used as the acid or amine component of the reaction are shown in Table 4. The same reaction can be performed by using a serine proteinase such as Subtilisin BPN'. As stated above, the synthesis of oligopeptides and polypeptides can be achieved by selecting the appropriate protective group for the carboxyl group of the amino component by using the thiol proteinase or the serine proteinase though they exhibit esterase and amidase action. The catalytic effect of the present enzymes for peptide synthesis is completely unexpected. As it is clear from the foregoing description, in the process of the present invention, the synthesis of peptides having the desired amino acid sequence can be attained by utilizing the characteristics of an endopeptidase. Only a catalytic amount of the enzyme is sufficient and the enzyme can be repeatedy used. The reaction proceeds smoothly under mild conditions in a buffer solution or in a solution having a desired pH. The yields are relatively high and the purity of the products is substantially high. The process of the invention can be utilized both in stepwise elongation of peptide chains and in condensation of peptide fragments. Both reactions are effective for industrial purposes. Moreover, racemization of the peptides does not occur, which is a result which could not be attained by the conventional synthetic methods.

Having generally described the invention, a more complete understanding can be obtained by reference to certain specific examples which are included for purpose of illustration only and are not intended to be limiting unless otherwise specified.

EXAMPLE 1

A mixture of 20 ml of McIlvaine buffer solution having a pH of 6.2 and 3 ml of methanol was added to 497 mg (1.20 mmol) of Z—Lys(Z)—OH and 366 mg (1.09 mmol) of H—Lys(Z)—OBu$^t$. Then, 130 mg of papain (titre 1200 CSU/g manufactured by Green-cross K.K.) and 0.05 ml of 2-mercapto ethanol were added to the mixture with stirring at 38° C for 24 hours, and the reaction was conducted. The resulting oily product was extracted with ethyl acetate and the extracted solution was sequentially washed with water, 0.5 N ACl, 7% ammonia water and water. The ethyl acetate solution was condensed and petroleum ether was added to the solution whereby 385 mg (48%) of crude crystals of Z—Lys(Z)—Lys(Z)—OBu' were obtained. A portion of the crystals was recrystallized from ethyl acetate-petroleum ether whereby a pure product having a melting point of 62 to 66° C and an $[\alpha]_D^{25} = -14.2°$ (C=0.5 methanol) was obtained.

| | ELEMENTAL ANALYSIS | | |
|---|---|---|---|
| | C | H | N |
| Calculated(%) | 65.55 | 7.15 | 7.65 |
| Found(%) | 65.55 | 7.22 | 7.67 |

EXAMPLE 2

A mixture of 20 ml of McIlvaine buffer solution having a pH of 7.0 and 4 ml of methanol was added to 692 mg (1.20 mmol) of Z—Arg(Z,Z)—OH and 470 mg (1.00 mmol) of H—Leu—OBzh.TosOH. Then, 150 mg of papain and 0.1 ml of 2-mercapto ethanol were added to the mixture with stirring at 38° C for 10 hours and the reaction was conducted. The resulting colorless precipitate was filtered and was sequentially washed with water, 7% ammonia water, and water whereby the product Z—Arg(Z,Z)—Leu—OBzh was obtained.

Yield 850 mg (99%). Melting point 161° to 168° C. $[\alpha]_D^{25} = -9.4°$ C (C=1.0 N,N-dimethylformamide)

| Elemental Analysis | C | H | N |
|---|---|---|---|
| Calculated (%) | 68.76 | 6.24 | 8.18 |
| Found (%) | 68.43 | 6.18 | 8.38 |

EXAMPLE 3

A 20 ml amount of McIlvaine buffer solution having a pH of 6.6 was added to 691 mg (2.00 mmol) of BOC-His(Bzl)-OH and 599 mg (1.80 mmol) of H—Leu—NHBzh.HCl. Then, 250 mg of papain and 100 mg of cysteine hydrochloride were added to the mixture with stirring at 38° C for 24 hours and the reaction was conducted. The resulting colorless precipitate was filtered and sequentially washed with water, 7% ammonia water and water whereby 750 mg of crude crystals were obtained. The product was dissolved in 50 ml of hot methanol and the hot solution was treated with activated carbon to remove protein. The solution was concentrated, water was added to the residue and the product was recrystallized whereby the crystalline product, BOC—His(Bzl)—Leu—NHBzh was obtained.

Yield 686 mg(62%). Melting point 113° to 115° C. $[\alpha]_D^{25} = -8.1°$ (C=1.0 chloroform)

| Elemental Analysis | C | H | N |
|---|---|---|---|
| Calculated % | 71.24 | 7.27 | 11.23 |
| Found (%) | 71.15 | 7.30 | 11.31 |

EXAMPLE 4

A 20 ml amount of McIlvaine buffer solution having a pH of 6.6 was added to 511 mg (2.00 mmol) of BOC—His—OH and 599 mg (1.80 mmol) of H-Leu-NHBzh.HCl. Then, 250 mg of papain and 100 mg of cysteine hydrochloride were added to the mixture with stirring at 38° C for 24 hours and the reaction was conducted. The resulting colorless precipitate was filtered and sequentially washed with water, 7% ammonia water and water whereby crude crystals of product were obtained. The product was dissolved in methanol water and the hot solution was treated with activated carbon to remove protein. The solution was concentrated whereby the crystalline product, BOC—His—Leu—NHBzh was obtained.

Yield 336 mg (35%). Melting point 221° to 223° C. $[\alpha]_D^{25} = -23.6°$ (C=0.5 chloroform)

| Elemental Analysis | C | H | N |
|---|---|---|---|
| Calculated (%) | 67.52 | 7.37 | 13.12 |
| Found (%) | 67.39 | 7.38 | 13.21 |

EXAMPLE 5

A 40 ml amount of McIlvain buffer solution having a pH of 6.2 was added to 531 mg (2.00 mmol) of BOC—Phe—OH and 935 mg (2.00 mmol) of H—His—(Bzl)—NHDMB.2HCl and then 4 ml of 1N NaOH was added to the solution. Then, 480 mg of papain and 240 mg of cysteine hydrochloride were added to the mixture with stirring at 38° C for 24 hours and the reaction was conducted. The resulting colorless precipitate was filtered and was sequentially washed with water, 7% ammonia and water, wherein 960 mg of crude crystals of product were obtained. The product was dissolved in 100 ml of hot methanol and the hot solution was treated with activated carbon for 30 minutes to remove protein. The solution was condensed and then water was added to the solution whereby the crystalline product of BOC—Phe—His(Bzl)—NHDMB.½H$_2$O was obtained.

Yield 650 mg (50%). Melting point 128° to 132° C. $[\alpha]_D^{25} = +1.6°$ (C=1.0 chloroform)

| Elemental Analysis | C | H | N |
|---|---|---|---|
| Calculated (%) | 66.44 | 6.82 | 10.76 |
| Found (%) | 66.34 | 6.66 | 10.78 |

EXAMPLES 6 to 23

The process of Example 1 was repeated except that the acid component of Nα-acylamino acid and the amine component of the amino acid ester of H—Val—OBzh were used as shown in Table 1. The results are shown in Table 1. The process of Example 1 was repeated except that the acid component of the Nα-acylamino acid of Z—Ala—OH and the amino component of the amino acid ester or amide were used as shown in Table 2. The results are shown in Table 2.

Table 1

| Example | Acid component | Amine component | Product | Yield (%) | Melting poing (° C) | Elementary Analysis ① calculated (%) ② found (%) | | | |
|---|---|---|---|---|---|---|---|---|---|
| | | | | | | | C | H | N | S |
| 6 | Z-Leu-OH | H-Val-OBzh | Z-Leu-Val-OBzh | 73 | oily | ① | 72.43 | 7.22 | 5.28 | |
| | | | | | | ② | 72.54 | 7.12 | 4.74 | |
| 7 | Z-Phe-OH | H-Val-OBzh | Z-Phe-Val-OBzh | 91 | 100–106 | ① | 68.98 | 6.71 | 4.66 | |

Table 1-continued

| Example | Acid component | Amine component | Product | Yield (%) | Melting point (°C) | | Elementary Analysis ① calculated (%) ② found (%) | | | |
|---|---|---|---|---|---|---|---|---|---|---|
| | | | | | | | C | H | N | S |
| 8 | Z-Ser-OH | H-Val-OBzh | Z-Ser-Val-OBzh | 34 | oily | ① | 71.21 | 6.34 | 4.80 | |
| | | | | | | ② | 69.03 | 6.39 | 5.55 | |
| 9 | Z-Thr-OH | H-Val-OBzh | Z-Thr-Val-OBzh | 66 | 89–95 | ① | 71.11 | 6.44 | 4.66 | |
| | | | | | | ② | 69.48 | 6.61 | 5.40 | |
| 10 | Z-Met-OH | H-Val-OBzh | Z-Met-Val-OBzh | 81 | 95–98 | ① | 69.19 | 6.59 | 5.26 | 5.84 |
| | | | | | | ② | 67.86 | 6.61 | 5.12 | 5.79 |
| | | | | | | | 67.83 | 6.60 | 5.16 | |
| 11 | Z-Asn-OH | H-Val-OBzh | Z-Asn-Val-OBzh | 25 | 116–125 | ① | 67.78 | 6.26 | 7.90 | |
| | | | | | | ② | 68.18 | 6.27 | 7.41 | |
| 12 | Z-Glu-OH | H-Val-OBzh | Z-Glu-Val-OBzh | 61 | 125–131 | ① | 68.12 | 6.27 | 5.12 | |
| | | | | | | ② | 68.23 | 6.31 | 4.84 | |
| 13 | Z-Glu-OH | H-Val-OBzh | Z-Glu-Val-OBzh | 69 | 178–183 | ① | 68.24 | 6.47 | 7.74 | |
| | | | | | | ② | 67.94 | 6.39 | 7.74 | |
| 14 | Z-Arg(NO₂)-OH | H-Val-OBzh | Z-Arg(NO₂)-Val-OBzh | 83 | 139–142 | ① | 62.12 | 6.19 | 13.58 | |
| | | | | | | ② | 62.98 | 6.21 | 13.40 | |
| 15 | Z-Lys(Z)-OH | H-Val-OBzh | Z-Lys(Z)-Val-OBzh | 70 | 110–117 | ① | 70.67 | 6.67 | 6.18 | |
| | | | | | | ② | 70.28 | 6.66 | 6.33 | |

Table 2

| Example | Acid component | Amine component | Product | Yield (%) | Melting point (°C) | | Elementary Analysis ① calculated (%) ② found (%) | | |
|---|---|---|---|---|---|---|---|---|---|
| | | | | | | | C | H | N |
| 16 | Z-Ala-OH | H-Val-OBzh | Z-Ala-Val-OBzh | 80 | 92–96 | ① | 71.29 | 6.60 | 5.73 |
| | | | | | | ② | 71.28 | 6.54 | 5.82 |
| 17 | Z-Ala-OH | H-Leu-OBuᵗ | Z-Ala-Leu-OBuᵗ | 49 | 95.5–97.0 | ① | 64.26 | 8.22 | 7.14 |
| | | | | | | ② | 64.65 | 8.15 | 7.14 |
| 18 | Z-Ala-OH | H-Phe-OBzh | Z-Ala-Phe-OBzh | 89 | 123–125 | ① | 73.86 | 6.01 | 5.52 |
| | | | | | | ② | 73.97 | 6.01 | 5.11 |
| 19 | Z-Ala-OH | H-Ile-OBzh | Z-Ala-Ile-OBzh | 92 | 88–96 | ① | 71.69 | 6.82 | 5.58 |
| | | | | | | ② | 71.72 | 6.83 | 5.44 |
| 20 | Z-Ala-OH | H-Ala-NHBzh | Z-Ala-Ala-NHBzh | 61 | 230–232 | ① | 70.57 | 6.36 | 9.14 |
| | | | | | | ② | 69.48 | 6.10 | 9.24 |
| 21 | Z-Ala-OH | H-Asn-NHBzh | Z-Ala-Asn-NHBzh | 53 | 252–254 | ① | 66.91 | 6.02 | 11.15 |
| | | | | | | ② | 66.70 | 6.11 | 10.92 |
| 22 | Z-Ala-OH | H-Arg(NO₂)-NHBzh | Z-Ala-Arg(NO₂)-NHBzh · ½H₂O | 52 | 123–125 | ① | 60.19 | 6.06 | 16.38 |
| | | | | | | ② | 60.06 | 6.10 | 16.42 |
| 23 | Z-Ala-OH | H-Lys(Z)-OBuᵗ | Z-Ala-Lys(Z)-OBuᵗ | 48 | 62–66 | ① | 65.55 | 7.15 | 7.65 |
| | | | | | | ② | 65.55 | 7.22 | 7.67 |

EXAMPLE 24

A 1.5 ml amount of N,N-dimethylformamide was added to 370 mg (1.20 mmol) of Z—Pro—Gly—OH and 305 mg (1.00 mmol) of H—Leu—NHBzh.½H₂O with stirring, and then 15 ml of citric acid buffer solution having a pH of 5.5 was added to the mixture. Then, 200 mg of papain and 0.2 ml of 2-mercapto ethanol were added to the mixture with stirring at 38° C for 24 hours and the reaction was conducted. The resulting colorless precipitate was filtered and was sequentially washed with water, 5% citric acid aqueous solution, water and 7% ammonia solution whereby 310 mg (51%) of crude crystals having a melting point of 146° to 149° C were obtained. The product was dissolved in methanol and a small amount of insoluble material was separated by filtration. The solution was concentrated and water was added to the residue whereby the product, Z—Pro—Gly—Leu—NHBzh.H₂O having a melting point of 148° to 150° C and an $[\alpha]_D^{25} = -41.0°$ (C=0.5 methanol) was obtained.

| Elemental Analysis | C | H | N |
|---|---|---|---|
| Calculated (%) | 67.75 | 7.02 | 9.30 |
| Found (%) | 68.05 | 6.96 | 9.24 |

EXAMPLES 25 to 32

The process of Example 24 was repeated except that an acid component of the Nα-acyldipeptide of Z-Phe-Ala-OH and an amine component of the amino acid or amide shown in Table 3 were used. The results are shown in Table 3.

Table 3

| Example | Acid component | Amine component | Product | Yield (%) | Melting point (°C) | | Elementary Analysis ① calculated (%) ② found (%) | | |
|---|---|---|---|---|---|---|---|---|---|
| | | | | | | | C | H | N |
| 25 | Z-Phe-Ala-OH | H-Gly-NHBzh | Z-Phe-Ala-Gly-NHBzh | 54 | 218–219 | ① | 70.92 | 6.12 | 9.45 |
| | | | | | | ② | 71.17 | 6.15 | 9.46 |
| 26 | Z-Phe-Ala-OH | H-Ala-NHBzh | Z-Phe-Ala-Ala-NHBzh · ½H₂O | 86 | 219–220 | ① | 70.22 | 6.38 | 9.10 |
| | | | | | | ② | 70.39 | 6.22 | 9.28 |
| 27 | Z-Phe-Ala-OH | H-Val-NHBzh | Z-Phe-Ala-Val-NHBzh | 37 | 258–259 | ① | 71.90 | 6.67 | 8.83 |
| | | | | | | ② | 71.97 | 6.69 | 8.89 |
| 28 | Z-Pro-Gly-OH | H-Ile-NHBzh | Z-Pro-Gle-NHBzh | 60 | 211–213 | ① | 69.84 | 6.90 | 9.58 |
| | | | | | | ② | 69.63 | 6.86 | 9.41 |
| 29 | Z-Pro-Gly-OH | H-Val-NHBzh | Z-Pro-Gly-Val-NHBzh · ½H₂O | 71 | 197–199 | ① | 68.37 | 6.78 | 9.67 |
| | | | | | | ② | 68.77 | 6.61 | 9.65 |
| 30 | Z-Pro-Gly-OH | H-Met-NHBzh | Z-Pro-Gly-Met-NHBzh | 93 | 190 | ① | 65.76 | 6.35 | 9.30 |
| | | | | | | ② | 65.61 | 6.38 | 9.46 |
| 31 | Z-Pro-Gly-OH | H-Arg(NO₂)- | Z-Pro-Gly-Arg(NO₂)- | 76 | 120–125 | ① | 60.70 | 5.99 | 16.66 |

Table 3-continued

| Example | Acid component | Amine component | Product | Yield (%) | Melting point (° C) | Elementary Analysis ① calculated (%) ② found (%) | | |
|---|---|---|---|---|---|---|---|---|
| | | | | | | C | H | N |
| 32 | Z-Pro-Gly-OH | NHBzh H-Asn-NHBzh | NHBzh Z-Pro-Gly-Asn-NHBzh | 80 | 239-240 | ② 60.65 ① 65.62 ② 65.62 | 6.23 6.02 6.00 | 16.53 11.96 12.01 |

EXAMPLE 33

A mixture of 15 ml of McIlvaine buffer solution having a pH of 8.0 and 15 ml of methanol was added to 564 mg (1.2 mmol) of BOC—Val—Tyr—(Bzl)—OH and 516 mg (1.0 mmol) of H—Val—His(Bzl)—OBzl.2HCl. Then, 300 mg of papain and 150 mg of cysteine hydrochloride were added to the mixture with stirring at 38° C for 24 hours and the reaction was conducted. The resulting colorless precipitate was filtered and was washed with water whereby 450 mg of crude crystals were obtained. The product was dissolved in 40 ml of ethanol and the hot solution was treated with activated carbon to remove protein. The solution was cooled and the resulting precipitate was filtered and the filtrate was condensed. The residue was recrystallized by adding ether to the residue whereby the product BOC—Val—Tyr(Bzl)—Val—His(Bzl)—OH was obtained.

Yield 100 mg (12%). Ninhydrin test negative. Melting point 159° to 165° C. $[\alpha]_D^{25} = -8.16°$ (C-0.5 N, N-dimethylformamide)

| Elemental Analysis | C | H | N |
|---|---|---|---|
| Calculated (%) | 63.44 | 7.26 | 10.00 |
| Found (%) | 63.67 | 7.04 | 10.24 |

EXAMPLE 34

A mixture of 20 ml of McIlvaine buffer solution having a pH of 6.1 and 10 ml of methanol were added to 518 mg (1.1 mmol) of BOC—Val—Tyr(Bzl)—OH and 583 mg (1.0 mmol) of H—Val—His(Bzl)—NHBzh.2HCl and then 2 ml of 1N NaOH was added to the solution. Then, 240 mg of papain and 120 mg of cysteine hydrochloride were added to the mixture with stirring at 38° C for 48 hours and the reaction was conducted. The resulting colorless precipitate was filtered and was sequentially washed with 0.5 N HCl, 7% of ammonia water, and water whereby 950 mg of crude crystals were obtained. The product was dissolved in 300 ml of methanol and the hot solution was treated with activated carbon to remove protein. The solution was concentrated and the residue was recrystallized from N,N-dimethylformamide-water whereby BOC—Val—Tyr(Bzl)—Val—His(Bzl)—NHBzh was obtained.

Yield 410 mg (42%). Melting point 237° to 239° C. $[\alpha]_D^{25} = -6.1°$ (C=1.0 N,N-dimethylformamide)

| Elemental Analysis | C | H | N |
|---|---|---|---|
| Calculated (%) | 69.84 | 7.10 | 10.00 |
| Found (%) | 70.18 | 7.01 | 9.94 |

EXAMPLES 35 to 41

The process of Example 34 was repeated except that an acid component of $N^\alpha$-acyldipeptide and an amine component of a dipeptide amide of H-Phe-Ser-NHBzh as shown in Table 4 were used. The results are shown in Table 4.

Table 4

| Example | Acid component | Amine component | Product | Yield (%) | Melting point (° C) | Elementary Analysis ① calculated (%) ② found (%) | | | |
|---|---|---|---|---|---|---|---|---|---|
| | | | | | | C | H | N | S |
| 35 | Z-Ala-Gly-OH | H-Phe-Ser-NHBzh | Z-Ala-Gly-Phe-Ser-NHBzh | 85 | 254-256 | ① 67.17 ② 67.02 | 6.08 5.94 | 10.30 10.36 | |
| 36 | BOC-Val-Gly-OH | H-Phe-Ser-NHBzh | BOC-Val-Gly-Phe-Sert-NHBzh . ½H₂O | 82 | 238-239 | ① 64.23 ② 64.27 | 7.14 7.05 | 10.12 10.26 | |
| 37 | BOC-Leu-Gly-OH | H-Phe-Ser-NHBzh | BOC-Leu-Gly-Phe-Ser-NHBzh | 79 | 195-202 | ① 66.35 ② 66.17 | 7.18 7.03 | 10.18 10.00 | |
| 38 | Z-Phe-Gly-OH | H-Phe-Ser-NHBzh | Z-Phe-Gly-Phe-Ser-NHBzh | 86 | 257-260 | ① 69.91 ② 69.97 | 6.00 6.22 | 9.27 9.46 | |
| 39 | Z-Pro-Gly-OH | H-Phe-Ser-NHBzh | Z-Pro-Gly-Phe-Ser-NHBzh | 61 | 228-230 | ① 68.07 ② 67.70 | 6.14 6.16 | 9.92 9.87 | |
| 40 | PMZ-Met-Gly-OH | H-Phe-Ser-NHBzh | PMZ-Met-Gly-Phe-Ser-NHBzh | 88 | 200-210 | ① 63.96 ② 64.11 | 6.15 6.23 | 9.10 9.04 | 4.16 4.16 |
| 41 | Z-Trp-Gly-OH | H-Phe-Ser-NHBzh | Z-Trp-Gly-Phe-Ser-NHBzh | 67 | 248-252 | ① 69.50 ② 69.44 | 5.83 5.95 | 10.57 10.73 | |

EXAMPLE 42

A mixture of 7.5 ml of McIlvaine buffer solution having a pH of 7.0 and 7.5 ml of methanol was added to 282 mg (0.6 mmol) of BOC—Val—Tyr—(Bzl)—OH and 345 mg (0.5 mmol) of H—Val—His( Bzl)—Pro—Phe—OEt.2HCl and then 1 ml of 1N NaOH was added. Thereafter, 150 mg of papain and 70 mg of cysteine hydrochloride were added to the mixture with stirring at 38° C for 24 hours and the reaction was conducted. The resulting colorless precipitate was filtered and was sequentially washed with water, 0.5 N HCl, 7% ammonia water and water whereby 400 mg of crude crystals of product were obtained. The product was dissolved in 50 ml of ethyl acetate and the hot solution was treated with activated carbon to remove protein. The solution was concentrated and the residue was recrystallized from methanol-water wherey Boc—Val—Tyr(Bzl)—Val—His(Bzl)—Pro—Phe—OEt was obtained.

Yield 226 mg (42). Ninhydrin test negative. Melting point 167° to 173° C. $[\alpha]_D^{25} = -34.0$ (C=1.0 N,N-dimethylformamide)

$= -56.1$ (C=1.0 methanol)

| Elemental Analysis | C | H | N |
|---|---|---|---|
| Calculated (%) | 66.82 | 7.19 | 10.39 |
| Found (%) | 66.72 | 7.16 | 10.55 |

The same product was produced by a solution method. The properties of the product are as follows:

Melting point: 164° to 174° C. Comelting point: 161° to 167° C. $[\alpha]_D^{25} = -35.3$ (C=1.0 N,N-dimethylformamide)

−59.2 (C=1.0 methanol)

The racemization of the product produced by the enzyme method was not found in comparison with the product obtained by the solution method.

EXAMPLE 43

A mixture of 15 ml of McIlvaine buffer solution having a pH of 8.0 and 15 ml of methanol was added to 943 mg (1.20 mmol) of BOC—Asn—Arg(NO₂)—Val—Tyr(Bzl)—OH and 690 mg (1.00 mmol) of H—Val—His(Bzl)—Pro—Phe—OEt.2HCl. Thereafter, 300 mg of papain and 150 mg of cysteine hydrochloride were added to the mixture with stirring at 38° C for 4 hours and the reaction was conducted. The resulting colorless precipitate was filtered and was sequentially washed with water, 0.5 N HCl, 7% ammonia and water whereby 1.20 g of crude crystals were obtained. The product was dissolved in 200 ml of ethanol and the solution was treated with activated carbon to remove protein. The solution was concentrated and the residue was recrystallized by adding ether whereby the crystalline product BOC—Asn—Arg(NO₂)—Val—Tyr(Bzl)—Val—His(Bzl)—Pro—Phe—OEt was obtained.

Yield 530 mg (37%). Melting point 185° to 197° C. $[\alpha]_D^{25} = -47.3°$ (C = 1.0 methanol). $[\alpha]_D^{25} = -25.3°$ (C = 1.0 N,N-dimethylformamide)

| Elemental Analysis | C | H | N |
|---|---|---|---|
| Calculated (%) | 59.17 | 6.88 | 14.79 |
| Found (%) | 59.11 | 6.62 | 15.02 |

The same product was produced by the solution method. The properties of the product are as follows.

Melting point 185° to 198° C. Comelting point 185° to 190° C. $[\alpha]_D^{25} = -48.4°$ (C = 1.0 methanol)

−26.5° (C = 1.0 N,N-dimethylformamide)

The racemization of the product produced by the enzyme method was not found in comparison with the product obtained by the solution method.

EXAMPLE 44

A 2 ml amount of N,N-diemthylformamide was added to 420 mg (1.50 mmol) of Z—Gln—OH and 480 mg (1.25 mmol) of H—Leu—OBzh.(COOH)₂ with stirring and then 20 ml of citric acid buffer solution having a pH of 5.5 was added to the mixture. Thereafter, 300 mg of Stembromelein and 0.2 ml of 2-mercapto ethanol were added to the mixture with stirring at 38° C for 24 hours and the reaction was conducted. The resulting colorless precipitate was filtered and was sequentially washed with water, 5% citric acid, water, 7% ammonia water and water whereby 680 mg (97%) of the product, Z—Gln—Leu—OBzh having a melting point of 158° to 163° C were obtained. After drying, the product was dissolved in methanol and the hot solution was treated with active carbon. The solution was concentrated and the residue was crystallized by adding water to the concentrate whereby a pure product having a melting point of 160° to 163° C and an $[\alpha]_D^{25} = -38.1°$ (C=1.0 methanol) was obtained.

| Elemental Analysis | C | H | N |
|---|---|---|---|
| Calculated (%) | 68.67 | 6.66 | 7.51 |
| Found (%) | 68.65 | 6.65 | 7.61 |

EXAMPLE 45

A 15 ml of citric acid buffer solution having a pH of 5.5 was added to 403 mg (1.20 mmol) of Z—Leu—Ala—OH and 310 mg (1.00 mmol) of H—Phe—OBuᵗ.(COOH)₂. Thereafter, 200 mg of Stembromelein and 0.2 ml of 2-mercapto ethanol were added to the mixture with stirring at 38° C for 24 hours and the reaction was conducted. The resulting colorless precipitate was filtered and was sequentially washed with water, 5% citric acid, water 7% ammonia and water whereby 310 mg of crude crystals of product were obtained. After drying, the product was dissolved with ethyl acetate and the solution was treated with activated carbon. The solution was concentrated and the residue was recrystallized from petroleum ether whereby the product. Z—Leu—Ala—Phe—OBuᵗ was obtained.

Yield 250 mg (4.6). Melting point 73° to 77° C. $[\alpha]_D^{25} = -40.0°$ (C=0.5 methanol)

| Elemental Analysis | C | H | N |
|---|---|---|---|
| Calculated (%) | 66.77 | 7.66 | 7.79 |
| Found (%) | 66.76 | 7.71 | 7.90 |

EXAMPLE 46

A 2 ml of N,N-dimethylformamide was added to 470 mg (1.40 mmol) of Z—Leu—Ala—OH and 585 mg (1.25 mmol) of H—Ile—OBzh.TosOH with stirring and then 20 ml of citric acid buffer solution having a pH of 5.5 was added to the mixture. Thereafter, 300 mg of Stembromelein and 0.2 ml of 2-mercapto ethanol were added to the mixture with stirring at 38° C for 24 hours and the reaction was conducted. The resulting colorless precipitate was filtered and was sequentially washed with water, 5% citric acid water, 7% ammonia solution and water whereby 610 mg (79%) of the product, Z—Leu—Ala—Ile—OBzh having a melting point of 167° to 170° C were obtained. The product was dissolved in ethyl acetate and the solution was treated with activated carbon. The solution was concentrated and the residue was recrystallized by adding ether to the concentrate whereby a pure product having a melting point of 170° to 171° C and an $[\alpha]_D^{25} = -60.2°$ (C=1.0 methanol) was obtained.

| Elemental Analysis | C | H | N |
|---|---|---|---|
| Calculated (%) | 70.22 | 7.37 | 6.82 |
| Found (%) | 69.95 | 7.40 | 6.91 |

EXAMPLES 47 to 56

The process of Example 46 was repeated except that the acid component of an Nα-acyl dipeptide and an amine component of the amino acid ester or amide shown in Table 5 were used.

The results are shown in Table 5.

Table 5

| Example | Acid component | Amine component | Product | Yield (%) | Melting point (°C) | | Elementary Analysis calculated (%) / found (%) | | |
|---|---|---|---|---|---|---|---|---|---|
| | | | | | | | C | H | N |
| 47 | PMZ-Ala-Ala-OH | H-Leu-OBzh | PMZ-Ala-Ala-Leu-OBzh | 93 | 117–118 | ① | 67.64 | 6.85 | 6.96 |
| | | | | | | ② | 67.83 | 6.90 | 6.95 |
| 48 | PMZ-Ala-Ala-OH | H-Asn-NHBzn | PMZ-Ala-Ala-Asn-NHBzn . ½H$_2$O | 54 | 270–273 | ① | 62.73 | 6.25 | 11.43 |
| | | | | | | ② | 62.80 | 6.18 | 11.60 |
| 49 | Z-Leu-Ala-OH | H-Leu-OBzh | Z-Leu-Ala-Leu-OBzh | 90 | 145–146 | ① | 70.22 | 7.37 | 6.82 |
| | | | | | | ② | 70.15 | 7.37 | 6.88 |
| 50 | Z-Leu-Ala-OH | H-Phe-NHBzh | Z-Leu-Ala-Phe-NHBzh | 63 | 227–230 | ① | 72.20 | 6.84 | 8.64 |
| | | | | | | ② | 72.29 | 6.81 | 8.63 |
| 51 | Z-Leu-Ala-OH | H-Asn-NHBzh | Z-Leu-Ala-Asn-NHBzh | 68 | 225–256 | ① | 66.32 | 6.71 | 11.38 |
| | | | | | | ② | 66.14 | 6.72 | 11.33 |
| 52 | Z-Phe-Ala-OH | H-Val-NHBzh | Z-Phe-Ala-Val-NHBzh | 47 | 258–259 | ① | 71.90 | 6.67 | 8.83 |
| | | | | | | ② | 71.97 | 6.69 | 8.89 |
| 53 | Z-Phe-Ala-OH | H-Phe-OBzh | Z-Phe-Ala-Phe-OBzh | 78 | 189–193 | ① | 73.77 | 6.04 | 6.15 |
| | | | | | | ② | 73.68 | 6.03 | 6.37 |
| 54 | Z-Phe-Ala-OH | H-Phe-OBu$^t$ | Z-Phe-Ala-Phe-OBu$^t$ | 52 | 118–122 | ① | 69.09 | 6.85 | 7.33 |
| | | | | | | ② | 69.17 | 7.00 | 7.45 |
| 55 | A-Ala-Leu-OH | H-Ala-NHBzh | Z-Ala-Leu-Ala-NHBzh . ½H$_2$O | 56 | 230–233 | ① | 68.13 | 7.11 | 9.63 |
| | | | | | | ② | 67.88 | 7.04 | 9.78 |
| 56 | Z-Ala-Leu-OH | H-Leu-OBzh | Z-Ala-Leu-Leu-OBzh | 77 | 110–111 | ① | 70.22 | 7.37 | 6.82 |
| | | | | | | ② | 70.41 | 7.42 | 6.92 |

EXAMPLE 57

A 2 ml amount of N,N-dimethylformamide was added to 380 mg (1.50 mmol) of Z—Thr—OH and 480 mg (1.25 mmol) of H—Leu—OBzh.(COOH)$_2$ with stirring and then 20 ml of citric acid buffer solution having a pH of 5.5 was added to the mixture. Thereafter, 300 mg of Ficin and 0.3 ml of 2-mercapto ethanol were added to the mixture with stirring at 38° C for 24 hours and the reaction was conducted. The resulting colorless precipitate was filtered and was sequentially washed with water, 5% citric acid, water, 7% ammonia water and water whereby 330 mg (50%) of the product, Z—Thr—Leu—OBzh having a melting point of 114° to 117° C were obtained. The product was dissolved in ethyl acetate and the solution was concentrated. The residue was recrystallized by adding ether to the concentrate whereby a pure product having a melting point of 120° to 122° C and an $[\alpha]_D^{25} = -41.4°$ (C=1.0 methanol) was obtained.

| Elemental Analysis | C | H | N |
|---|---|---|---|
| Calculated (%) | 69.90 | 6.81 | 5.26 |
| Found (%) | 70.02 | 6.87 | 5.16 |

EXAMPLE 58

A 1.5 ml amount of N,N-dimethylformamide was added to 320 mg (1.20 mmol) of BOC—Met—OH and 254 mg (1.00 mmol) of H—Ala—NHBzh with stirring. Then, 15 ml of citric acid buffer solution having a pH of 5.5 was added to the mixture. Thereafter, 300 mg of Ficin and 0.3 ml of 2-mercapto ethanol were added to the mixture with stirring at 38° C for 24 hours and the reaction was conducted. The resulting colorless precipitate was filtered and was sequentially washed with water, 5% citric acid, water, 7% ammonia water and water, whereby 400 mg (82%) of the product BOC—Met—Ala—NHBzh having a melting point of 163° to 164° C were obtained. The product was dissolved with ethyl ether and the solution was concentrated. The residue was recrystallized from ether-petroleum ether whereby a pure product having a melting point of 159° to 161° C and an $[\alpha]_D^{25} = -29.6°$ (C=1.0 methanol) was obtained.

| Elemental Analysis | C | H | N |
|---|---|---|---|
| Calculated (%) | 64.30 | 7.26 | 8.65 |
| Found (%) | 64.13 | 7.20 | 8.77 |

EXAMPLE 59

A 2 ml amount of N,N-dimethylformamide was dissolved in 516 mg (1.40 mmol) of Z—Phe—Ala—OH and 480 mg (1.25 mmol) of H—Leu—OBzh.(COOH)$_2$ with stirring and then 20 ml of citric acid buffer solution having a pH of 5.5 was added. Thereafter, 200 mg of Ficin and 0.2 ml of 2-mercapto ethanol were added to the mixture with stirring at 38° C for 24 hours and the reaction was conducted. The resulting colorless precipitate was filtered and was sequentially washed with water, 5% citric acid, water, 7% ammonia water and water whereby 540 mg (67%) of crude crystals having a melting point of 156° to 158° C were obtained. The product was dissolved in methanol and a small amount of insoluble material was removed. The solution was concentrated and the residue was recrystallized by adding water whereby the product, Z—Phe—Ala—Leu—OBzh having a melting point of 151° to 152° C and $[\alpha]_D^{25} = -47.4°$ (C = 0.5 methanol) was obtained.

| Elemental Analysis | C | H | N |
|---|---|---|---|
| Calculated (%) | 72.09 | 6.67 | 6.47 |
| Found (%) | 71.84 | 6.66 | 6.63 |

EXAMPLE 60

A mixture of 20 ml of McIlvaine buffer solution having a pH of 6.2 and 3 ml of methanol was added to 370 mg (1.26 mmol) of Z—Phe—OH and 360 mg (1.07 mmol) of H—Lys(Z)—OBu$^t$. Thereafter, 130 mg of papain and 0.05 ml of 2-mercapto ethanol were added to the mixture with stirring at 38° C for 20 hours. The resulting colorless precipitate was filtered and was sequentially washed with water, 0.5 M citric acid, 7% ammonia water and water. The resulting crude crystals were dissolved in ethyl acetate and the hot solution was treated with activated carbon. Thereafter, n-hexane was added to the filtrate whereby the product, Z—Phe—Lys(Z)—OBu$^t$ was obtained.

Yield 531 mg (80%). Melting point 118° to 121° C. $[\alpha]_D^{25} = -13.5°$ (C = 1.0 methanol)

| Elemental Analysis | C | H | N |
|---|---|---|---|
| Calculated (%) | 68.05 | 7.02 | 6.80 |
| Found (%) | 68.19 | 6.98 | 6.85 |

EXAMPLE 61

A mixture of 20 ml of McIlvain having a pH of 6.2 and 3 ml of methanol was added to 359 mg (1.20 mmol) of Z—Phe—OH and 173 mg (1.00 mmol) of H—Val—OBu$^t$. Then, 130 mg of papain and 0.05 ml of 2-mercapto ethanol were added to the mixture at 38° C for 20 hours and the reaction was conducted. The resulting oily product was dissolved in ethyl actate and the solution was sequentially washed with water, 0.5 N HCl, 7% ammonia water and water. The solution was dried and treated with activated carbon to remove protein. The solution was concentrated and the petroleum ether was added to the concentrate whereby the crystalline product Z—Phe—Val—OBu$^t$ was obtained.

Yield 315 mg (69%). Melting point 104° to 106° C. $[\alpha]_D^{25} = -19.0°$ C (C=1.0 methanol)

The melting point and $[\alpha]_D^{25}$ agreed with the data disclosed in (Chem. Ber. 100,160 (1967)).

The following are reference procedures for converting the peptides produced by the process of the invention to the corresponding free compounds.

REFERENCE EXAMPLE 1

A 2.00 g (3.20 mmol) amount of Z—Phe—Lys(-Z)—OBu$^t$ was dissolved in 15 ml of ethyl acetate and was admixed with 20 ml of 6.0 N HCl-ethyl acetate. The reaction was conducted at room temperature for 2 hours and the solution was concentrated. Dried ether was added to the residue whereby Z—Phe—Lys (Z)—OH was obtained.

Yield 1.69 g (94%). Melting point 94° to 96° C. $[\alpha]_D^{25} = -6.2°$ (C = 0.5 methanol)

| Elemental Analysis | C | H | N |
|---|---|---|---|
| Calculated (%) | 66.29 | 6.28 | 7.48 |
| Found (%) | 65.93 | 6.02 | 7.71 |

REFERENCE EXAMPLE 2

A 909 mg (2.00 mmol) amount of Z—Phe—Val—OBu$^t$ was dissolved in a mixture of 8 ml of methanol and 0.12 ml of acetic acid and was admixed with 100 mg of 10% Pd-C. The reaction was carried out for 2 hours in a hydrogen atmosphere and then the catalyst was filtered. Methanol was removed by distillation and the residue was dissolved in ethyl acetate. The solution was washed with an aqueous solution of sodium bicarbonate and water. The ethyl acetate solution was dried and concentrated and petroleum ether was added to it whereby the crystalline produce H—Phe—Val—OBu$^t$ was obtained.

Yield 612 mg (96%). Melting point 65° to 67° C $[\alpha]_D^{25} = -30.0°$ (C=1.0 methanol)

The melting point and $[\alpha]_D^{25}$ agreed with the data disclosed in (Chem. Ber. 100, 160 (1967).

EXAMPLE 62

A 20 ml amount of Kolthoff buffer solution having a pH of 8.5 was added to 409 mg (1.10 mmol) of BOC—TYr(Bzl)—OH and 303 mg (1.00 mmol) of H—Val—NHDMB.HCl and then, 1.0 ml of 1N NaOH was added to the mixture. Thereafter, 100 mg of serine proteinase (titre 100 × 10$^4$ PUN/g sold by Nagase Sangyo K.K.) was added to the mixture with stirring at 38° C for 24 hours and the reaction was conducted. The gel precipitate was filtered and was sequentially washed with water, 0.5 N HCl, 7% ammonia water and water, whereby 361 mg of crude crystals of product were obtained. The product was dissolved in methanol and the hot solution was treated with activated carbon to remove protein. The solution was concentrated and the product was recrystallized by adding water whereby the pure product BOC—Tyr(Bzl)—Val—NHDMB was obtained.

Yield 297 mg (48%). Melting point 165° to 168° C. $[\alpha]_D^{25} = -0.8°$ (C=0.25 chloroform)

| Elemental Analysis | C | H | N |
|---|---|---|---|
| Calculated (%) | 67.83 | 7.32 | 6.78 |
| Found (%) | 67.71 | 7.35 | 6.60 |

EXAMPLE 63

A 20 ml amount of citric acid buffer solution having a pH of 7.5 was added to 518 mg (1.10 mmol) of BOC—Val—Tyr(Bzl)—OH and 517 mg (1.00 mmol) of H—Val—His(Bzl)—OBzl.2HCl and then 2.0 ml of 1N NaOH was added to the solution. Then, 100 mg of the serine proteinase of Example 62 was added to the mixture with stirring at 38° C for 24 hours and the reaction was conducted. The resulting colorless precipitate was filtered and was washed with water whereby 620 mg of crude crystals were obtained. The product was dissolved in 300 ml of hot methanol and the hot solution was treated with activated carbon for 1 hour to remove protein. The solution was concentrated and water was added to the residue whereby the crystalline product BOC—Val—Tyr(Bzl)—Val—His(Bzl)—OH.H$_2$O was obtained.

Yield 450 mg (56%). Melting point 176° to 180° C $[\alpha]_D^{25} = -6.6°$ (C=0.5 methanol)

| Elemental Analysis | C | H | N |
|---|---|---|---|
| Calculated (%) | 64.84 | 7.17 | 10.31 |
| Found (%) | 64.84 | 7.16 | 10.90 |

EXAMPLE 64

A 7.5 ml amount of McIlvaine buffer solution having a pH of 8.97 was added to 282 mg (0.60 mmol) of BOC—Val—Tyr(Bzl)—OH and 345 mg (0.50 mmol) of H—Val—His(Bzl)—Pro—Phe—OEt.2HCl and then 1.2 ml of 1N NaOH was added to the solution. Thereafter, 40 mg of serine proteinase was added to the mixture with stirring at 38° C for 24 hours and the reaction was conducted. The resulting gel precipitate was filtered and was sequentially washed with water, 0.5 N HCl and water whereby 400 mg of crude crystals of product were obtained. The product was dissolved in hot ethanol and the hot solution was treated with activated carbon to remove protein. The solution was concentrated and the residue was recrystallized from ethyl acetate whereby the product of BOC—Val—Tyr(Bzl)—Val—His(Bzl)—Pro—Phe—OH.2H$_2$O was obtained.

Yield 334 mg (62%). Melting point 163° to 168° C. [α]$_D^{25}$ = −26.9° (C=1.0 N,N-dimethylformamide)

| Elemental Analysis | C | H | N |
|---|---|---|---|
| Calculated (%) | 64.66 | 7.11 | 10.40 |
| Found (%) | 64.87 | 6.80 | 10.52 |

EXAMPLES 65 to 70

The process of Example 64 was repeated except that an acid component of an N$^\alpha$-acylamino acid or N$^\alpha$-acyl dipeptide and an amine component of the dipeptide t-butyl esters shown in Table 6 were used.

Table 6

| Example | Acid component | Amine component | Product | Yield (%) | Melting point (° C) | | Elementary Analysis calculated (%) ① found (%) ② C | H | N |
|---|---|---|---|---|---|---|---|---|---|
| 65 | Z-Leu-OH | H-Phe-Val-OBu$^t$ | Z-Leu-Phe-Val-OBu$^t$ | 46 | 106–108 | ① | 67.70 | 7.99 | 7.40 |
| | | | | | | ② | 67.87 | 7.99 | 7.39 |
| 66 | Z-Leu-Phe-OH | H-Phe-Val-OBu$^t$ | Z-Leu-Phe-Phe-Val-OBu$^t$ | 82 | 180–184 | ① | 68.88 | 7.71 | 7.84 |
| | | | | | | ② | 68.75 | 7.66 | 7.98 |
| 67 | Z-Phe-Tyr-OH | H-Phe-Val-OBu$^t$ | Z-Phe-Tyr-Phe-Val-OBu$^t$ . ½H$_2$O | 35 | 158–166 | ① | 68.29 | 6.90 | 7.24 |
| | | | | | | ② | 68.43 | 6.81 | 7.04 |
| 68 | Z-Phe-Val-OH | H-Phe-Val-OBu$^t$ | Z-Phe-Val-Phe-Val-OBu$^t$ | 22 | 181–186 | ① | 68.55 | 7.48 | 7.99 |
| | | | | | | ② | 68.33 | 7.50 | 8.00 |
| 69 | Z-Phe-Arg(NO$_2$)-OH | H-Phe-Val-OBu$^t$ | Z-Phe-Arg(NO$_2$)-Phe-Val-OBu$^t$ | 21 | 105–116 | ① | 61.33 | 6.78 | 13.96 |
| | | | | | | ② | 61.42 | 6.79 | 13.14 |
| 70 | Z-Phe-Ser-OH | H-Lys(TOS)-Phe-OBu$^t$ | Z-Phe-Ser-Lys(TOS)-Phe-OBu$^t$ | 59 | 168–172 | ① | 62.08 | 6.68 | 7.88 |
| | | | | | | ② | 61.82 | 6.60 | 7.74 |

EXAMPLE 71

In a flask, 280.2 mg (1 mmol) of Z—Gln—OH and 368.5 mg (1 mmol) of H—Phe—Phe—OBu$^t$ were suspended in 10 ml of water. The glass electrode of a pH meter was inserted into the suspension. A 150 mg amount of papain and 0.1 ml of 2-mercapto ethanol were added to the suspension with stirring while the pH of the mixture was adjusted to about 5.0 by adding 1/10 N NaOH to dissolve the solid components. The mixture was stirred at 38° C for 20 hours and the reaction the was conducted. During the reaction, pH of the reaction mixture was maintained at 5 to 6 by adding 1/10 N NaOH while measuring the pH of the reaction mixture with a pH meter. The resulting precipitate was filtered and was sequentially washed with water, 1N HCl, water, 7% ammonia water and water and was dried. The product was recrystallized from ethyl acetate whereby 510 mg of the product of Z—Gln—Phe—Phe—OBu$^t$ having a melting point of 197° to 200° C were obtained.

Yield 80.8%. [α]$_D^{25}$ = −18.3° (C=1.0 N,N-dimethylformamide)

| Elemental Analysis (C$_{35}$H$_{42}$O$_7$N$_4$) | C | H | N |
|---|---|---|---|
| Calculated (%) | 66.65 | 6.71 | 8.80 |
| Found (%) | 66.51 | 6.71 | 8.74 |

EXAMPLE 72

In a flask, 398.5 mg of Z—Phe—Val—OH and 320.4 mg of H—Phe—Val—OBu$^t$ were suspended in 10 ml of water. The glass electrode of a pH meter was inserted into the suspension. A 150 mg amount of papain and 0.1 ml of 2-mercapto ethanol were added to the suspension with stirring while adjusting the pH of the mixture to about 4.5 to 5.0 by adding a diluted HCl solution to dissolve the solid components. The mixture was stirred at 38° C for 20 hours and the reaction was conducted. During the reaction, the pH of the reaction mixture was maintained at 4.5 to 5.0 by adding a diluted HCl solution to the reaction mixture. The resulting precipitate was filtered and was sequentially washed with water, 1N HCl, water, 7% ammonia water, and water and was dried. The product was recrystallized from ethyl acetatepetroleum ether whereby 30 mg (yield 4.3%) of the product Z—Phe—Val—Phe—Val—OBu$^t$ having a melting point of 130 to 145° C were obtained.

EXAMPLE 73

In a flask, 398.5 mg (1 mmol) of Z—Phe—Val—OH and 320.4 mg (1 mmol) of H—Phe—Val—OBu$^t$ were suspended in 10 ml of water. The glass electrode of a pH meter was inserted into the suspension. A 150 mg amount of serine proteinase was added to the suspension with stirring while adjusting the pH of the mixture to 7.5 to 8.0 by adding a 1/10 N NaOH solution dropwise to the solution to dissolve the solid components. The mixture was stirred at 38° C for 20 hours and the reaction was conducted. During the reaction, the pH of the mixture was maintained at 7.5 to 8 by adding 1/10 N NaOH to the mixture while measuring the pH of the reaction mixture with a pH meter. The resulting precipitate was filtered and was sequentially washed with water, 1N HCl, water, 7% ammonia water and water and was dried. The product was recrystallized from ethyl acetate-petroleum ether whereby 190 mg (yield of 27.1%) of the product of Z—Phe—Val—OBu$^t$ having a melting point of 130° to 145° C were obtained.

EXAMPLE 74

In a flask, 471.5 mg (1 mmol) of Z—Phe—Tyr—OH and 320.4 mg of H-Phe—Val—OBu$^t$ were suspended in 10 ml of water. The glass electrode of a pH meter was inserted into the suspension. A 150 mg amount of serine proteinase was added to the suspension with stirring while adjusting the pH of the mixture to 7.5 to 8.0 by adding 1/10 N NaOH to the mixture to dissolve the solid components. The mixture was stirred at 38° C for 20 hours and the reaction was conducted. During the reaction, the pH of the reaction mixture was maintained at 7.5 to 8.0 by adding 1/10 N NaOH to the mixture. The resulting precipitate was filtered and sequentially washed with water, 1N HCl, water, 7% ammonia water and water and was dried. The product was recrystallized from ethyl acetate-petroleum ether whereby 230 mg (yield of 30%) of the product, Z—Phe—Tyr—Phe—Val—OBu$^t$ having a melting point of 155° C was obtained.

Having now fully described the invention, it will be apparent to one of ordinary skill in the art that many changes and modifications can be made thereto without departing from the spirit or scope of the invention as set forth herein.

What is claimed as new and intended to be secured by Letters Patent is:

1. A process for producing a peptide having the formula

X—A—B—Y wherein
A and B are the same or different and represent an amino acid residue or a peptide residue;
X represents an amino protective group; and
Y represents a carboxyl protective group selected from the group consisting of tertiary alkoxy, and benzyloxy, benzylamino and benzhydrylamino which can be substituted with an inert substituent, which comprises:
reacting an acid component of an amino acid or peptide having N-terminal protective group or a salt thereof of the formula X-A-OH with an amino component of an amino acid or peptide having a C-terminal protective group or a salt thereof of the formula

H—B—Y in the presence of a thiol proteinase or serine proteinase enzyme in an aqueous solution having a pH sufficient to maintain the enzyme activity of said thiol proteinase or serine proteinase.

2. The process of claim 1, wherein said thiol proteinase is papain, Stembromelein, Ficin, Cathepsin B, Chymopapain, or Streptococcal proteinase and said serine proteinase is subtilisin, Aspergillus alkaline proteinase, Elastase, α-Lytic proteinase or Chymotryspin.

3. The process of claim 1, wherein the pH is maintained at a sufficient level by reacting the amino acid or peptide reactants in a buffer solution at a pH of 4 to 7.5 for the thiol proteinase and 6 to 9 for the serine proteinase.

4. The process of claim 1, wherein the pH is maintained at the desired level by detecting the pH of the reaction mixture and adding an acid or a base to said aqueous solution depending upon the measured pH of the reaction mixture.

5. The process of claim 1, wherein the reaction is conducted with a reactant ratio of 0.8 to 2 moles of the acid component per mole of the amine component.

6. The process of claim 1, wherein the reaction is conducted by adding 10 to 500 mg of said thiol proteinase or serine proteinase to said solution per mmole of said amine component.

7. The process of claim 1, wherein the N-terminal protective group of the acid component is a tertiary alkoxycarbonyl group or a benzyloxycarbonyl group which can be substituted with an inert substituent, p-toluenesulfonyl or o-nitrophenyl sulfenyl, and the C-terminal protective group of the amine component is tertiary alkoxy, benzyloxy (—OBzl), p-nitrobenzyloxy [—OBzl (p-NO$_2$)], benzhydryloxy, (—OBzh), benzylamino (—NHBzl), 2,4-dimethoxybenzylamino (—NHDMB), benzhydrylamino(—NHBzh) which can be substituted with an inert substituent.

8. The process of claim 7, wherein said tert-alkoxycarbonyl group is t-butyloxycarbonyl, or t-amyloxycarbonyl; said substituted benzyloxycarbonyl is p-methoxybenzyloxycarbonyl, 3-5-dimethoxybenzyloxycarbonyl, p-phenylazobenzyloxycarbonyl, or 2,4,6-trimethylbenzyloxycarbonyl, said tertiary alkoxy group is t-butoxy, and said inert substituent of said benzyhydrylamino group is 2,4-dimethoxyoxybenzylamino or benzyhydrylamino.

9. The process of claim 1, wherein A and B are the same or different and represent an amino acid residue or peptide residue wherein the amino acid is an aliphatic amino acid, an oxyamino acid, a sulfur-containing amino acid, a monoamino dicarboxylic acid, a diamino monocarboxylic acid, an aromatic amino acid or a heterocyclic amino acid.

10. The process of claim 9, wherein said aliphatic amino acid is a monoaminomonocarboxylic selected from the group consisting of glycine, alanine, valine, norvaline, leucine, isoleucine, and norleucine, said oxyamino acid is serine, threonine or homoserine; said sulfur-containing amino acid is methionine, cystine or cysteine; said monoamino dicarboxylic acid is aspartic acid or glutamic acid; said diamino monocarboxylic acid is ornithine, lysine, or arginine; said aromatic amino acid is phenylalanine or tyrosine, and said heterocyclic amino acid is histidine or tryptophan.

* * * * *

UNITED STATES PATENT AND TRADEMARK OFFICE
CERTIFICATE OF CORRECTION

PATENT NO. : 4,086,136
DATED : April 25, 1978
INVENTOR(S) : Isowa et al

It is certified that error appears in the above-identified patent and that said Letters Patent are hereby corrected as shown below:

Please insert the following:

--[30] Foreign Application Priority Data

October 23, 1975   Japan..............50-126876
    October 23, 1975   Japan..............50-126878--

Signed and Sealed this

Seventh Day of November 1978

[SEAL]

Attest:

RUTH C. MASON
Attesting Officer

DONALD W. BANNER
Commissioner of Patents and Trademarks